United States Patent [19]

Ratcliff

[11] Patent Number: 4,925,656

[45] Date of Patent: May 15, 1990

[54] METHOD FOR RETARDING FORMATION OF DENTAL PLAQUE

[76] Inventor: Perry A. Ratcliff, 7125 E. Lincoln Dr., Scottsdale, Ariz. 85253

[21] Appl. No.: 279,421

[22] Filed: Dec. 2, 1988

Related U.S. Application Data

[60] Division of Ser. No. 88,609, Aug. 24, 1987, Pat. No. 4,818,519, which is a continuation-in-part of Ser. No. 24,329, Mar. 10, 1987, Pat. No. 4,837,009, which is a continuation-in-part of Ser. No. 947,079, Dec. 29, 1986, Pat. No. 4,689,215, which is a continuation of Ser. No. 846,342, Mar. 31, 1986, abandoned, which is a continuation of Ser. No. 636,027, Jul. 30, 1984, abandoned, and Ser. No. 17,241, Dec. 29, 1986, Pat. No. 4,696,811, said Ser. No. 846,342.

[51] Int. Cl.$^5$ .................... A61K 7/20; A61K 33/20
[52] U.S. Cl. ............................... 424/53; 424/661
[58] Field of Search .................... 424/53, 661

[56] References Cited

U.S. PATENT DOCUMENTS

| | | | |
|---|---|---|---|
| 2,451,897 | 10/1948 | Woodward | 99/111 |
| 2,482,958 | 9/1949 | Woodward | 99/150 |
| 2,546,568 | 3/1951 | Taylor | 99/150 |
| 2,711,363 | 6/1955 | Waibel | 23/85 |
| 2,871,097 | 1/1959 | Rapson | 23/152 |
| 3,084,995 | 4/1963 | Grubitsch | 23/152 |
| 3,147,124 | 9/1964 | Wentworth | 99/116 |
| 3,271,242 | 9/1966 | McNicholas | 167/17 |
| 3,322,497 | 5/1967 | Martin | 23/152 |
| 3,585,147 | 6/1971 | Gordon | 252/187 |
| 3,591,515 | 7/1971 | Lovely | 252/187 |
| 3,593,494 | 7/1971 | Durrell | 55/51 |
| 3,754,079 | 8/1973 | Callerame | 423/479 |
| 3,828,097 | 8/1974 | Callerame | 423/472 |
| 4,104,190 | 8/1978 | Hartshorn | 252/187 |
| 4,247,531 | 1/1981 | Hicks | 423/477 |
| 4,250,144 | 2/1981 | Ratigan | 422/112 |
| 4,250,159 | 2/1981 | Cowley | 423/480 |
| 4,292,292 | 9/1981 | Hicks | 423/477 |
| 4,330,531 | 5/1982 | Alliger | 424/149 |
| 4,362,707 | 12/1982 | Hardee et al. | 423/478 |
| 4,381,290 | 4/1983 | Hardee et al. | 423/478 |
| 4,396,592 | 8/1983 | Combroux | 423/478 |
| 4,414,193 | 10/1983 | Fredette et al. | 423/478 |

OTHER PUBLICATIONS

*Time* magazine, Sep. 9, 1985, article entitled "Today's Dentistry, a New Drill", pp. 73 and 74.

*Chlorine Dioxide* by W. J. Masschelein, pub. Ann Arbor Science Publishers, Inc., ©1979, pp. 139–140 and footnotes 110 to 116.

Brochure entitled "Purogene, the Magic of Oxyfresh, Issues and Answers", Brochure entitled Oxyfresh, Questions and Answers.

Article entitled "Controlled Clinical Evaluations of Chlorine Dioxide, Chlorite and Chlorate in Man", vol. 46, pp. 59–62 of 1982 issue of Environmental Health Perspectives.

*Primary Examiner*—Shep K. Rose
*Attorney, Agent, or Firm*—Cahill, Sutton & Thomas

[57] ABSTRACT

The use of stabilized chlorine dioxide or chlorine dioxide in aqueous solution as a composition to reduce or prevent plaque formation and treatment of oral diseases ecologically plaque dependent, such as gingivitis and periodontitis, is disclosed. Preferred concentrations are in the range of 0.005% to 0.2% and the chlorine dioxide may be in the form of a rinse, a wash, a soak or a dentrifrice.

2 Claims, No Drawings

METHOD FOR RETARDING FORMATION OF DENTAL PLAQUE

REFERENCE TO RELATED APPLICATIONS

This is a division of Ser. No. 088,609, filed Aug. 24, 1987, now U.S. Pat. No. 4,818,519, which is a continuation in part of Ser. No. 024,329, filed Mar. 10, 1987, now U.S. Pat. No. 4,837,009, which is a continuation in part of Ser. No. 947,079, filed Dec. 29, 1986, now U.S. Pat. No. 4,689,215, which is a continuation of Ser. No. 846,342, filed Mar. 31, 1986, now abandoned, which is a continuation of Ser. No. 636,027, filed Jul. 30, 1984, abandoned, and Ser. No. 017,241, filed Dec. 29, 1986, now U.S. Pat. No. 4,696,811, which is a continuation of Ser. No. 846,342, filed Mar. 31, 1986, now abandoned, which is a continuation of Ser. No. 636,027, Jul. 30, 1984, now abandoned.

BACKGROUND OF THE INVENTION:

1. Field of the Invention

The present invention is directed to a method and composition for prevention and treatment of oral disease and more particularly, to the use of a chlorine dioxide in aqueous solution for preventing formation of plaque and treatment of plaque dependent diseases.

2. Description of the Prior Art

The volatile sulfur compounds, hydrogen sulfide ($H_2S$) methylmercaptan ($CH_3SH$) and di-methylmercaptan ($CH^3$)$_2S$ are recognized in the current dental literature as being the major contributors to oral malodor. Numerous researchers using organoleptic, chemical, amperometric, mass spectrometric, or gas liquid chromatographic methods have demonstrated that these volatile sulfur compounds are present in the head space and vapor of putrefied saliva and in individual samples of mouth air. In most persons, hydrogen sulfide and methylmercaptan constitute over 90% of the total volatile sulfur content identified in mouth air.

These malodorous volatile sulfur compounds are generated primarily through the putreficative action of oral microorganisms on sulfur containing amino acids, peptones or proteins found in the mouth. These subtrates are readily available in saliva and dental plaque or may be derived form proteinaceous food particles trapped between the teeth, in the gingival crevice or adhering to the mucous membranes and the irregular surface of the tongue as well as exfoliated oral epithelium, food debris and the like. Current studies have indicated that mouth odor not only comes from the posterior dorsal surface of the tongue but also from periodontal pockets. People with periodontal involvement have an attendant increase in oral malodor from disintegrated epithelial cells.

Starting with a clean tooth surface, plaque formation and resulting ecology occurs in the following steps:

1. Deposition of a coating of glycoproteins from salivary and other oral mucous gland secretions. This is referred to as acquired pellicle.

2. Fastening and colonization of streptococcus organisms to the acquired pellicle, primarily by streptococcus sanguis and streptococcus mutans.

3. Conversion of sucrose to glucans (dextran) and fructans by the bacterial enzyme glucosyltransferases. In this plaque mass are imbedded dead cells, cell debris and food debris. High molecular weight polymers of glucose and other sugars, altered salivary glycoproteins, proteases and various chemotactic and inflammatory inducing substances have been detected and partially characterized.

4. Other organisms, primarily gram positive aerobes, become residents in the plaque mass and use the glucans and fructans for nutrition. These are primarily oxygen using organisms and the oxygen source is from the saliva that bathes the plaque mass.

5. With time and the functioning of this ecological system, the oxygen use by the superficial bacteria deprive the lower layers of the plaque matrix of a supply of oxygen. An opportunity for non-oxygen using bacteria (facultative anaerobes) to become established is provided.

6. If left undisturbed, the ecological system now established is self perpetuating. That is, the streptococcus bacteria continue to produce glucans and fructans. Other bacteria produce toxins that kill cells of the host and the dead cells become other essential nutrients. The superficial bacteria deprive the deeper layers of the plaque mass of oxygen and keep the ecological system going. Thus, both aerobic and anaerobic organisms survive in the plaque mass.

7. The established ecological system attendant the plaque mass produces toxins from the aerobic bacteria that cause gingivitis and toxins from the anaerobic bacteria that cause periodontitis.

Various substances have been tested for their ability to disrupt plaque or prevent its formation and to treat mouth odor such as antibiotics, chlorhexdines, oxine, and alexidine.

The prior art compositions that have been used and tested, have found some acceptance but are generally inefective in periodontitis, gingivitis, plaque accumulation and mouth malodor. Accordingly, there exists a clear need for composition which will effectively inhibit the initial pellicle which precedes plaque formation and inhibit or control the formation of bacterial plaque and suppress organisms such as but not limited to (1) Streptococcus Mutans, which is implicated as the major cause of human dental decay; (2) Black Pigmented Bacteriodes, an Actinobacillus Actinomycetumcomitans which is implicated in human periodontitis; and (3) will reduce odor intensity in the mouth through the control of hydrogen sulfide and methylmercaptan.

SUMMARY OF THE PRESENT INVENTION

Broadly, the present invention contemplates the use of stabilized chlorine dioxide in aqueous solution for the treatment of the mouth as a deodorizing agent, anti-plaque agent, bactericide for treatment of gingivitis and periodontitis and as a bactericidal fungicidal and viralcidal agent in other related applications. In the present invention a composition containing stabilized chlorine dioxide may be used for treatment of the mouth either in a solution, for example, as a mouthwash or in a dentifrice generally in concentrations of below approximately 0.2% for the control of odorgenic microorganisms, bacterial plaque, gingivitis and bacteria which cause these conditions. Similarly, chlorine dioxide is also effective as a cellular debridgement agent following surgical procedures and sanitizer denture soak. The use of chlorine dioxide and its effects on man has been clinically evaluated. The relative safety of oral ingestion of chlorine dioxide was demonstrated extensively in animals and latter in humans by Lubbers, Chauan, and Bianchine, *Environmental Health Perspectives*, Volume 46, Pages 57-62, 1982.

DESCRIPTION OF PREFERRED EMBODIMENTS

Chlorine dioxide, $ClO_2$, functions biochemically in many ways other than as a germicide. These functions include: (1) oxidation of double bonds between two carbon atoms; (2) oxidation of unsaturated fatty acids (lipids) via double bonds between two carbon atoms; (3) acceleration of hydrolysis of carboxalic anhydrides; (4) oxidation of aldehydes to the corresponding carboxalic acids; (5) oxidation of alcohols; (6) oxidation of amines; (7) oxidation of phenols, phenolic derivatives and thiophenolic compounds; (8) moderate oxidation of hydroquinones; (9) oxidation of thiophenols; (10) Oxidation of amino acids, proteins and polyamides, primarily by attacking sulphide bonds. These are cystine, methionone and tryrosine. Tryptophane also has been shown to be reactive. Keratin, (which makes up the cyto-skeletal structure in epithelial cells cytoplasm), and $ClO_2$ keratin sulfonic hydrosoluble acids; (11) carbohydrates are altered at the CHO and $CH_2OH$ radicals to produce carboxylic functions; and (12) Nitrates and sulphides are readily oxidized.

The chlorine dioxide described herein is of the type referred to as stabilized chlorine dioxide. U.S. Pat. No. 3,271,242 describes a form of stabilized chlorine dioxide and a method of making it which is particularly useful in carrying out the present invention. Further discussion of stabilized chlorine dioxide in a form contemplated by the present invention may be found in a treatise entitled *Chlorine Dioxide* by W. J. Masschelein and published by the Ann Arbor Science Publishers, Inc., copyright 1979 (note in particular pages 138-140). Various embodiments of chlorine dioxide for various purposes are also reviewed in this treatise.

The first step in the formation of plaque on a clean tooth surface is the formation of acquired pellicle. Studies by others have shown the following to be part of the acquired pellicle formative process. Glycoproteins of salivary and other mucous gland origin are attached to the hydroxyapatite crystals. (Roukima, P. A. and Nieuw Amerongen, A. V., Sulphated Glycoproteins in Human Saliva; *Saliva and Dental Caries*, (Sp. Supp. Microbiology Abst.) 1979, pp 76. Embery, G., The role of anionic glyco-conjugates, particularly Sulphated Glycoproteins in relation to the Oral Cavity, *Saliva and Dental Caries*, (Supp. Microbiol Abstr.), Information Retrieval 1978, pp 105-111). Sulphated glycoproteins have a strong affinity to the calcium anion (ibid., pp 105-108). Most major salivary secreted glycoproteins may be bound to certain ester sulphates (ibid). These sulphated glycoproteins have been related to bacterial agglutination or clumping (ibid., pp 108).

Clinical observations by the inventor have led to the discovery that the process of acquired pellicle can be inhibited by the use by humans of stabilized chlorine dioxide as a rinse. Through such observations is has been learned that the chlorine dioxide reacts with the sulphated glycoproteins to inhibit pellicle formation. This process results primarily from, but is not limited to, oxidation of the sulphide bonds. Since acquired pellicle is the first step in plaque formation, this initial inhibition alters the sequence of events to follow. The second step, bacterial adhesion and subsequent steps are consequently retarded. No disulphate enzymes capable of cleaning the sulphate moieties of glycoproteins are known.

Bacterial agglutinigation includes the conversion of sucrose to glucans and fructans by enzymes known as glycosyltransferases. These enzymes are of bacterial origin. The plaque mass becomes a complex extra cellular (of microorganisms) matrix containing sulphated glucosamineglycans, proteoglycans, glycoproteins, sugar, proteins and lipids which aid in the process of bacterial agglutination (Schluger, S., Yuodelis, R. and Page, R., *Periodontal Disease*, Chapter 6, pp. 135-166, 1977, Lea & Febiger, Phila., Pa. Newbrun, E., Polyusaccharide Synthesis in Plague; *Microbiol Aspects of Dental Caries*, Vol III, (Supp. Microbiology Abstr.), 1976, pp 649-664). These compounds include the presence of sulphur and become unstable in the presence of high oxygen compounds. The oxygen splits the sulphide bonds to form sulphates or $SO_2$.

Clinical observations by the inventor have led to the conclusion that all of these biochemical compounds are attacked to a greater or lesser extent by stabilized chlorine dioxide. Since these compounds may be used as nutrients for bacteria, the reduction of the compounds will inhibit bacterial growth. More specifically, the stabilized chlorine dioxide oxidizes carbohydrates, chondroitin sulphates, glucosaminglycans, glycoproteins, proteins and lipids. Since these compounds arise as bacterial by products and debris from dead and dying cells, are of salivary origin and are the mechanism of agglutination of the plaque mass, their degradation/oxidation retards plaque growth.

The initial bacterial residents of the plaque mass are aerobic, oxygen using organisms. The saliva bathing the plaque matrixes the source of oxygen. As the plaque thickens, the deeper layers have a reduced oxygen content. The thicker the aerobic population of plaque matrix, the lower the oxygen level in the saliva. This permits the deeper layers of the plaque matrix to develop an anaerobic population of bacteria (Globerman, D. Y., and Kleinberg, I., Intra-Oral $PO_2$ and It's Relation to Bacterial Accumulation on the Oral Tissues; *Saliva and Dental Caries*, (Sp. Supp. Microbiology Abstr.) 1976 pp. 275-292).

Clinical observations by the inventor lead to the discovery that use of stabilized chlorine dioxide as a mouth rinse will rise the level of oxygen in the saliva. The raised level of oxygen within the plaque matrix will inhibit anaerobic bacterial growth. As periodontitis is caused by anaerobic bacteria, the potential for the development of periodontitis is reduced by stabilized chlorine dioxide as a rinse.

The inhibition of acquired pellicle formation, the prevention of bacterial agglutinization and the oxidization of the plaque mass through rinsing with chlorine dioxide in aqueous solution are independent of the germicidal capacity of such solution. Furthermore, these factors in combination with the bacteriocidal capacity of chlorine dioxide in aqueous solution renders the solution an effective pellicle and plaque inhibitor.

The permeability of sublingual mucous, tissue within the mouth is increased substantially by exposure to hydrogen sulfide ($H_2S$) and methyl mercaptan ($CH_3SH$). (Gaffer and Rizzo papers referenced in "Effect of Hydrogen Sulfide and Methyl Mercaptan on the Permeability of Oral Mucosa, *J. Dent Res.* 63(7), Jul. 1984, pages 994-997). Accordingly, the toxic bacterial products attendant plaque which produce these compounds have a related effect on tissue permeability.

Since chlorine dioxide breaks the di-sulphide bonds of both these compounds, the use of chlorine dioxide in aqueous solution as a mouthwash would reduce the penetration potential of pathogenic materials. Evidence exists that endotoxin and lipopolysaccharide from gram negative bacteria are the worst of the products to penetrate the tissues. Application of endotoxin to gingiva has caused gingival inflammation. (ibid).

Chlorine dioxide in aqueous solution used in treatment of plaque acts upon attendant gram negative bacteria. Thereby, the inventor has learned through experimentation and observation that Chlorine dioxide can be a preventive product leading to oral health.

EXAMPLE I

Deodorizing Mouthwash

In effort to find a suitable control agent for mouth odor, attention was directed towards the use of chlorine dioxide. The characteristics of stabilized chlorine dioxide which make it especially useful is that it is antiseptic, a bactericide, generally colorless, odorless, highly stable and has not apparent detrimental or deleterious effect on humans at the concentrations involved. As pointed out above, mouth malodor is primarily caused by volatile sulfur compounds, such as hydrogen sulfide, methylmercaptan and dimethyl mercaptan. As pointed out above, these chemicals are produced as degradation products of microorganisms acting on exogenous and endogenous proteinaceous substrates, oral epithelium, food debris and saliva. In order to control mouth odor, a deodorizing mouth wash consisting of a solution of 0.02% chlorine dioxide in deionized water was utilized as a rinse. Evidence indicates efficacy at lesser dilutions to 0.005% with more rapid effect at dilutions to 0.2%. Sulfides are readily oxidized by chlorine dioxide. Bacteria implicated in the production of malodor were also effectively controlled. Inhibition of these microorganisms will reduce dental plaque formation and maintenance process.

The chlorine dioxide mouthwash or rinse solution serves to attack production and origin of malodor from the mouth by splitting the sulfide bonds of both hydrogen sulfide and methylmercaptan. Therefore, delivery of stabilized chlorine dioxide provides reduction and elimination of these odors. Further, the bacteriostatic, bactericidal, fungistatic and fungicidal activity of stabilized chlorine dioxide will reduce the number of microorganisms which assist in the production of oral debris leading to disintegration of the organic compounds ultimately producing hydrogen sulfide and methylmercaptan. The known organisms include staphylococci, *B. Subtilis, B. Byrocaneous, Colon bacilli*, Black Pigmented Bacteriodes, Clostridia, *B. sporogenes, B. histolyticum*, and *T. mucosum*.

The mouthwash may be delivered as a simple rinse which bathes the tongue. Literature indicates that over 50% of mouth odor originates on the mouth and tongue surface, particularly the posterior dorsal surface of the tongue. Accordingly, a rinse is an effective treatment. However, persons with periodontal involvement may have an increase in oral malodor from disintegrated epithelial cells. A mouth rinse will not penetrate to attack gingival crevicular odorizers. To optimize treatment with a mouthwash containing stabilized chlorine dioxide, the wash must be delivered into the periodontal pockets as well as dorsal and lingual surfaces of the tongue. The preferred treatment to accomplish this is achieved by inserting the delivery tip of a syringe into the pockets or gingival crevices or by administering the wash by a mechanically powered water irrigating device such as one of the type sold under the trademark "Water Pik", manufactured by Teledyne Corp. Following irrigation, the user can swish the wash throughout the mouth, covering the dorsal surface of the tongue and other areas.

To improve the taste and appearance of the chlorine dioxide solution, appropriate sweeteners and colorings such as saccharin, peppermint and FTC #3 coloring agent may be added as is common with commercially available mouthwashes and is well-known to those in the art.

Evaluation of Mouthwash Containing Chloride Dioxide for its Effect on Volatile Sulfur Compounds The test mouthwash which had a concentration of 0.05%, was dispersed in ⅜ oz. aliquots in individual plastic containers. The study was performed over a 3-hour period on six human subjects with objectionable early morning concentrations of volatile sulfur compounds (VSC) greater than 0.5 ng $CH_3SH$/10 ml mouth air.

Rinsing Procedure: Following initial early morning VSC analysis on the day of evaluation, subjects were instructed to rinse, with vigorous swishing of rinse between teeth, for 30 seconds with ⅜ oz volumes of the test mouthwash. After the rinse was expectorated, the mouth was rinsed for 30 seconds with 15 ml of 18 megavolt pure water.

VSC Analysis: All VSC analysis were performed in duplicate on each subject at the following times:

1. Initial screening to select subjects with objectionable early morning concentrations of VSC.

2. On the day of evaluation, analysis were performed on early morning mouth air samples before rinsing. These values served as controls. Thus, each subject served as his own control against which the effect of the rinse was calculated. Immediately following these analysis, the subjects rinsed and were re-analyzed, 3 min., 13 min., one hour, two hours and 3 hours post-rinsing. The results are summarized on the following table:

TABLE 8

| | | | | | | | | | | | | | |
|---|---|---|---|---|---|---|---|---|---|---|---|---|---|
| | | | SUMMARY MOUTH AIR VSC REDUCTION | | | | | | | | | | |
| | | | | One Hour | | | | Two Hour | | | | Three Hour | |
| | Early Morning | | | % | | | % | | % | | % | | % |
| Subject | $H_2S$* | $CH_3SH$* | $H_2S$* | Red. | $CH_3SH$* | Red. | $H_2S$* | Red. | $CH_3SH$* | Red. | $H_2S$* | Red. | $CH_3SH$* | Red. |
| F. 1 | 0.82 | 0.72 | 0.39 | 52.44 | 0.37 | 48.61 | 0.39 | 52.44 | 0.59 | 18.06 | 0.75 | 8.54 | 1.08 | +50 |
| F. 2 | 1.30 | 1.04 | 0.29 | 77.69 | 0.17 | 83.65 | 0.41 | 68.46 | 0.24 | 76.92 | 0.45 | 65.38 | 0.23 | 72.88 |
| F. 3 | 0.98 | 0.77 | 0.77 | 21.43 | 0.57 | 25.97 | 0.69 | 29.59 | 0.52 | 32.47 | 0.82 | 16.33 | 0.62 | 19.48 |
| F. 4 | 0.73 | 1.04 | 0.39 | 46.58 | 0.2 | 75.00 | 0.37 | 49.32 | 0.31 | 70.19 | 0.47 | 35.62 | 0.46 | 55.76 |
| F. 5 | 1.56 | 0.88 | 0.58 | 62.82 | 0.41 | 53.41 | 0.75 | 51.92 | 0.40 | 54.55 | 0.86 | 44.87 | 0.80 | 9.09 |
| F. 6 | 1.12 | 1.41 | 0.40 | 64.29 | 0 | 100 | 0.41 | 63.39 | 0 | 100 | 0.55 | 50.89 | 0.43 | 69.50 |

Average

TABLE 8-continued

| | | SUMMARY MOUTH AIR VSC REDUCTION | | | | | | | | | | |
|---|---|---|---|---|---|---|---|---|---|---|---|---|
| | | | One Hour | | | Two Hour | | | | Three Hour | | |
| | Early Morning | % | | % | | % | | % | | % | | % |
| Subject | $H_2S$* CH$_3$SH* | $H_2S$* | Red. | CH$_3$SH* | Red. | $H_2S$* | Red. | CH$_3$SH* | Red. | $H_2S$* | Red. | CH$_3$SH* Red. |
| % Reduction | | | 54.21 | | 64.44 | | 52.52 | | 58.70 | | 36.94 | 30.25 |

*mg/10 ml volume of mouth air

The effectiveness of chlorine dioxide was tested both in vivo and in vitro and demonstrated that stabilized chlorine dioxide will kill at the 99% level in ten seconds streptococcus mutans, the principle organism implicated in the etiology of dental caries as well as other strains of organisms as demonstrated by the following tests:

| IN VITRO<br>THE BACTERICIDAL EFFECT OF $ClO_2$<br>AGAINST *STREPTOCOCCUS MUTANS* | | | | |
|---|---|---|---|---|
| | 200 ppm $ClO_2$ | | SURVIVED | |
| pH of Medium | Treatment Seconds | Organisms/0.2 ml | No. Organisms | % Kill |
| 4.80 | 5 | 40,000 | 68 | 99.83 |
| | 10 | 40,000 | 16 | 99.96 |
| | 20 | 40,000 | 5 | 99.99 |
| 5.95 | 5 | 40,000 | 1336 | 99.66 |
| | 10 | 40,000 | 98 | 99.76 |
| | 20 | 40,000 | 101 | 99.75 |
| 5.01 | 5 | 29,600 | *TNTC | 0.0 |
| | 10 | 29,600 | 125 | 99.58 |
| | 20 | 29,600 | 70 | 99.76 |
| 6.06 | 5 | 29,600 | *TNTC | 0.0 |
| | 10 | 29,600 | *TNTC | 0.0 |
| | 20 | 29,600 | 122 | 99.59 |
| 5.06 | 5 | 9,400 | 744 | 92.1 |
| | 10 | 9,400 | 176 | 98.1 |
| | 20 | 9,400 | 44 | 99.5 |
| 6.02 | 5 | 9,400 | 1248 | 86.7 |
| | 10 | 9,400 | 920 | 90.2 |
| | 20 | 9,400 | 640 | 93.2 |

*Too numerous to count

| THE BACTERICIDAL EFFECT OF $ClO_2$<br>AGAINST *BACTEROIDES GINGIVALIS* | | | | |
|---|---|---|---|---|
| | 200 ppm $ClO_2$ | | SURVIVED | |
| pH of Medium | Treatment Seconds | Organisms/0.2 ml | No. Organisms | % Kill |
| 5.21 | 5 | 53 | 0 | 100 |
| | 10 | 53 | 0 | 100 |
| | 20 | 53 | 0 | 100 |
| 5.96 | 5 | 53 | 0 | 100 |
| | 10 | 53 | 0 | 100 |
| | 20 | 53 | 0 | 100 |

| THE BACTERICIDAL EFFECT OF $ClO_2$<br>AGAINST *BACTEROIDES MELANINOGENICUS* | | | | |
|---|---|---|---|---|
| | 200 ppm $ClO_2$ | | SURVIVED | |
| pH of Medium | Treatment Seconds | Organisms/0.2 ml | No. Organisms | % Kill |
| 5.3 | 5 | 100,000 | 100,000 | 0 |
| | 10 | 100,000 | 100,000 | 0 |
| | 20 | 100,000 | 5,000 | 95 |
| 6.15 | 5 | 100,000 | 50,000 | 50 |
| | 10 | 100,000 | 50,000 | 50 |
| | 20 | 100,000 | 0 | 100 |
| 4.97 | 5 | 100,000 | 100,000 | 0 |
| | 10 | 100,000 | 100,000 | 0 |
| | 20 | 100,000 | 3,000 | 97 |
| 5.86 | 5 | 100,000 | 50,000 | 50 |
| | 10 | 100,000 | 0 | 100 |
| | 20 | 100,000 | 0 | 100 |
| 4.99 | 10 | 10,000 | 10,000 | 0 |
| | 20 | 10,000 | 0 | 100 |
| | 30 | 10,000 | 0 | 100 |
| 6.29 | 10 | 10,000 | 5,000 | 50 |
| | 20 | 10,000 | 0 | 100 |
| | 30 | 10,000 | 0 | 100 |

| THE BACTERICIDAL EFFECT OF $ClO_2$<br>AGAINST *BACTEROIDES MELANINOGENICUS* | | | | |
|---|---|---|---|---|
| | 200 ppm $ClO_2$ | | SURVIVED | |
| pH of Medium | Treatment Seconds | Organisms/0.2 ml | No. Organisms | % Kill |
| 4.97 | 10 | 10,000 | 10,000 | 0 |
| | 20 | 10,000 | 0 | 100 |
| | 30 | 10,000 | 0 | 100 |
| 5.85 | 10 | 10,000 | 3,000 | 70 |
| | 20 | 10,000 | 0 | 100 |
| | 30 | 10,000 | 0 | 100 |
| 4.97 | 5 | 8,560 | *TNTC | 0 |
| | 10 | 8,560 | 312 | 96.3 |
| | 20 | 8,560 | 67 | 99.2 |
| 5.87 | 5 | 8,560 | *TNTC | 0 |
| | 10 | 8,560 | 2 | 99.9 |
| | 20 | 8,560 | 1 | 99.9 |

*Too Numerous to Count

Materials and Methods

Materials used in all experiments:
1.0 AC 5215 Odorid, $ClO_2$ 1000 ppm, Biocide Chemical Co. Norman Ok
1.1 Chlorine-free distilled water employed throughout
1.2 Stirring apparatus, magnetic mixer with magnetic bar; IEC Centrifuge 6000
1.3 Petri plates (12×50 mm, 15×100 mm)
1.4 HCl 0.1 N. NaOH 0.1 N
1.5 Sodium thiosulfate solution 15%, employed 0.04 ml
1.6 Orthotolidine (o-toluidine) JT Baker, Baker Grde, boiling point 200°–201° C.
  $C_4$, $C_6$, $H_4$, $HN_2$, Standard Methods for Examination of Water and Wastewater, 14th Ed. 1975 Neutral Orthotolidine Regent, 0.04 ml employed
1.7 Diluent, saline with 0.5% Tween 80

Materials used in individual experiments:
1.0 Exp. Streptococcus mutans ATCC #27152
1.1 Brain Heart Infusion Broth employed for initial culture
1.2 Plate counts performed on plate count agar.
2.0 Exp. Bacteroides gingivalis ATCC #33277

2.1 Anaerobic Tryptic Soy Agar (TSA) with 5% sheep blood employed for initial isolation.
2.2 Plate counts were performed on anaerobic TSA with 5% horse serum
3.0 Exp. Bacteroides melaninogenicus ATCC #15930
3.1 Anaerobic TSA with 5% sheep blood was employed throughout
3.2 Extended time interval for stirring of organisms was 30 seconds
4.0 Exp. *Actinobacillus actinomycetuemocomitans* ATCC #29522
4.1 Initial cultures prepared on chocolate agar
4.2 Plate counts were performed on anaerobic TSA without sheep blood Methods:

Initially each ATCC culture employed was grown on the media documented under each organism. After isolation, all cultures were maintained on appropriate media. The initial bacterial count was determined by plating ten-fold serial dilutions of the selected organism in its respective medium. After incubation, the bacterial colonies were counted and 0.2 ml of the selected dilution was employed against $ClO_2$. $ClO_2$ was employed at 200 ppm. 0.8 ml of $ClO_2$ was mixed with 0.2 ml of organisms suspension and mao=mixed for the selected length of time in seconds: 5, 10, 20 and 30. Two organism-$ClO_2$ mixtures were mixed by a 45° tilting rotation in a small tube for the selected period of time.

In each experiment, subsequent to each mixing time of $ClO_2$ organism-mixtures, excess $CiO_2$ was neutralized by the addition of 0.04 ml of sodium thiosulfate. To assure complete neutralization of excess $ClO_2$ has occurred, 0.04 orthotolidine was added to each $ClO_2$-organism-sodium thiosulfate mixture. When $ClO_2$ is neutralized, the mixture remains clear. If residual $ClO_2$ is present, the mixture turn yellow after the addition of orthotolidine. Additional controls to determine the effect of each reagent singly or in combination against each organism include solidum thiosulfate-organism mixtures and sodium thiosulfate orthotolidine organism mixtures. A control plate count without reagents was included for each organism.

All cultures except *Streptococcus mutans* were grown anaerobically in CO at 37° C. for 48-96 hours. *Streptococcus mutans* were grown aerobically at 37° C. for 48 hours.

In Vivo

Chlorine Dioxide Evaluation

Thirty-nine periodontal pockets in twenty-nine patients were examined by dark field and phase microscopy. The motility and density of bacteria were evaluated from zero to three with zero being no activity and three very active.

Of the thirty-nine teeth thirty were molars, three were bicuspids and six were in the anterior region. Pocket dept ranged from 4 to 12 millimeters.

The patients were instructed to use a 0.1% chlorine dioxide solution twice daily. Four of the patients used chlorine dioxide as a mouth rinse and twenty-five used it as an irrigant with monoject 412 twelve cc syringe. The findings follow:

| | | | | | CLINICAL EFFECT OF .1% CHLORINE DIOXIDE | | | |
|---|---|---|---|---|---|---|---|---|
| TOOTH # | CODE # | SURFACE | BEFORE PHASE | AFTER PHASE | % CHANGE | BEFORE DARK FIELD | AFTER DARK FIELD | % CHANGE |
| 14 | 001 | M | 2 | 0 | 100% | 3 | 1+ | 50% |
| 23 | 001 | D | + | 0 | 100% | 2 | + | 75% |
| 30 | 002 | D | 0 | 0 | 0% | 1 | 0 | 100% |
| 18 | 003 | D | 2 | 0 | 100% | 2+ | 1− | 70% |
| 15 | 004 | L | + | 0 | 100% | + | + | 0% |
| 18 | 004 | D | 2 | 0 | 100% | 2+ | 1 | 60% |
| 14 | 005 | M | 2 | 1 | 50% | 2 | 2 | 0% |
| 30 | 005 | L | 1 | 0 | 100% | 2 | 0 | 100% |
| 15 | 006 | L | 0 | 0 | 0% | 2 | 0 | 100% |
| 19 | 007 | D | 0 | 0 | 0% | 3 | 0 | 100% |
| 31 | 008 | B | 2 | 0 | 100% | 2+ | 0 | 100% |
| 7 | 009 | D | 3 | 0 | 100% | 3 | 2 | 33% |
| 2 | 010 | M | 1 | 0 | 100% | 2 | 0 | 100% |
| 4 | 011 | M | 0 | 0 | 0% | 2 | 0 | 100% |
| 15 | 011 | D | 1 | 0 | 100% | 3 | 1− | 75% |
| 3 | 012 | M | 2 | 1− | 63% | 3 | 2 | 33% |
| 14 | 012 | M | 2 | 1 | 50% | 3 | 2 | 33% |
| 18 | 013 | M | 0 | 0 | 0% | 3 | 1 | 67% |
| 3 | 014 | M | 0 | 0 | 0% | 1 | 0 | 100% |
| 2 | 015 | M | 2 | 1 | 50% | 3 | 2 | 33% |
| 2 | 015 | D | 2 | + | 75% | 3 | + | 83% |

| | | | | | CLINICAL EFFECT OF .1% CHLORINE DIOXIDE | | | |
|---|---|---|---|---|---|---|---|---|
| TOOTH # | CODE # | SURFACE | BEFORE PHASE | AFTER PHASE | % CHANGE | BEFORE DARK FIELD | AFTER DARK -FIELD | % CHANGE |
| 21 | 016 | D | 0 | 0 | 0% | 2+ | 0 | 100% |
| 14 | 017 | M | 1 | 0 | 100% | 3 | 2 | 33% |
| 3 | 018 | M | 1 | 0 | 100% | 1 | 0 | 100% |
| 32 | 019 | D | 1+ | 0 | 100% | 2 | 0 | 100% |
| 31 | 020 | B | 2 | + | 75% | 3 | + | 83% |
| 2 | 021 | M | 2+ | 1 | 60% | 3 | 2 | 33% |
| 32 | 022 | D | 1 | 0 | 100% | 1 | + | 50% |
| 31 | 023 | M | 1 | 0 | 100% | 3 | 0 | 100% |
| 3 | 024 | D | 2 | 0 | 100% | 2 | 0 | 100% |

-continued

CLINICAL EFFECT OF .1% CHLORINE DIOXIDE

| TOOTH # | CODE # | SURFACE | BEFORE PHASE | AFTER PHASE | % CHANGE | BEFORE DARK FIELD | AFTER DARK FIELD | % CHANGE |
|---|---|---|---|---|---|---|---|---|
| 15 | 025 | D | 2 | 0 | 100% | 3 | 1 | 67% |
| 26 | 025 | D | 0 | 0 | 0% | 3 | 1 | 67% |
| 4 | 026 | M | 2 | 0 | 100% | 2+ | 1− | 70% |
| 12 | 026 | M | 1 | + | 50% | 3 | + | 83% |
| 8 | 027 | B | 1 | 0 | 100% | 2 | 1 | 50% |
| 3 | 028 | M | 1 | 0 | 100% | 3 | 1 | 67% |
| 31 | 029 | M | 1 | + | 50% | 3 | 1+ | 50% |
| 11 | 030 | D | + | 0 | 100% | 1 | + | 50% |

Evaluation Data

| Phase (Thirty Pockets with Activity) | | |
|---|---|---|
| Number of Pockets | % Resolution | % of Total |
| 21 | 100% | 70% |
| 2 | 75% | 6.67% |
| 1 | 63% | 3.33% |
| 1 | 60% | 3.33% |
| 5 | 50% | 16.07 |

Mean resolution (All Bacterial activity stopped or was reduced).

| Dark Field (Thirty-nine pockets with Activity) | | |
|---|---|---|
| Number of Pockets | % Resolution | % of Total |
| 14 | 100% | 35.89% |
| 3 | 83% | 7.69% |
| 2 | 75% | 5.13% |
| 2 | 70% | 5.13% |
| 4 | 67% | 10.26% |
| 1 | 60% | 2.56% |
| 5 | 50% | 12.82% |
| 6 | 33% | 15.38% |

(Two of the pockets exhibited no reduction in bacteria after the use of Chlorine Dioxide)

EXAMPLE II

Toothpaste

As demonstrated above, stabilized chlorine dioxide can be an effective agent on odor producing microorganisms and enzymes. However, the effectiveness of chlorine dioxide can be enhanced when included as an ingredient of a toothpaste. Toothpaste is more effective than a rinse or removing malodor from the gums or gingiva. The action of the brush dislodges, dead cells and putrescent debris from the gingival crevices as well as on the various mouth surfaces and on the tongue. The chlorine dioxide contained in the toothpaste acts as discussed above to prevent malodor and serve as a deodorizer by attacking hydrogen sulfide and methylmercaptan. A typical toothpaste would have the following composition: stabilized chlorine dioxide approximately 0.005% to 0.2%; detergent polishing agent; calcium carbonate or silica gel; flavoring; saccharin; peppermint; coloring agent. These other ingredients may vary and are the basic ingredients in many toothpastes as is well-known to those in the art. Other formulations including chlorine dioxide as the active ingredient would work as well.

EXAMPLE III

Anti-Plaque Agent

Dental plaque, as mentioned above, is formed by a combination of actions beginning with acquired pellicle from saliva coating the tooth and a subsequent adhesion to the coating by streptococcus organisms. S. Mutans degrade sucrose into glucose or fructose which are then compounded into dextrans and levans. The dextrans act as a nutrient substrate for the growth of additional organisms and the production of acids which demineralize tooth enamel and dentin causing tooth decay. The stabilized chlorine dioxide reacts with sulphated glycoproteins to inhibit or reduce pellicle formation through oxidation of the sulphide bonds. Streptococcus sanguis more frequently than streptococcus mutans will adhere to pellicle to provide dextrans by way of glucocyl-transferases. Chlorine dioxide is lethal to streptococcus mutans in vitro and materially reduces their numbers in vivo. The reduction of motility and mytosis by chlorine dioxide will reduce the amount of plaque formation. Dental plaque formation subsequent to any acquired pellicle is reduced when the microbial content of the mouth is reduced. Thus chlorine dioxide is an effective anti-microbial agent which functions as a dental plaque inhibitor or retardant and as an anti-cariogenic agent. Preferred concentrations are in the range from 0.005% to 0.2% in aqueous solutions as for example, in deionized water with suitable coloring and flavorings for patient comfort.

EXAMPLE IV

Anti-Gingivitis, Anti-Periodontitis And Gingival Bleeding Preventative

Gingivitis and the various forms of periodontitis are known to be caused by bacteria. Principal forms implicated are Black Pigmented Bacteroides and *Actinobacillus Actinomycetumcomitans*. Gingivitis occurs from toxins produced by the aerobic bacteria in coronal dental plaque and periodontitis occurs from toxins produced by anaerobic bacteria in infection extending into periodontal pockets or spaced between the gingiva (gums) and the tooth root. Thus, control of gingivitis is by oxidation of compounds produced as bacterial by products that otherwise would be the mechanism of agglutination of the plaque mass in the coronal dental plaque and control of periodontitis by raising the level of oxygen in the saliva to raise the level of oxygen in the plaque matrix and inhibit anaerobic bacterial growth in the plaque matrix found in the gingival crevices and elsewhere.

By the use of an oxidizing agent of the strength of chlorine dioxide in the mouth it will increase the amount of aerobic bacterial population which will prevent the accumulations of anaerobic populations in the higher oxygen tension. Since the anaerobes stimulate the immune reaction, which include lymphocyte cloning and subsequent release of the compliment cascade to induce inflammation and bone loss, the chlorine dioxide will help prevent periodontitis through it's higher oxygen tension created in the saliva. Further in this particular application, the higher oxygen tension will provide more oxygen available to convert the adjacent tissues from anaerobic into aerobic glycolysis. This will increase the number of adenosinetriphosphate molecules to increase the energy available for adjacent cells. The covering epithelial cells are the source of intracellular cementing glycoproteins and proteoglycans. If the cells do not have enough oxygen to function in aerobic glycolysis, there will be 1/18 the ATP production and with it the interference of active transport (delivery of nutrition to the cells) as well as cell adhesion to hold an effective covering and minimize bacterial penetration into the underlying connective tissues.

Clinical evidence had documented improvement in treatment of the above diseases when stabilized chlorine dioxide is used. The organisms currently implicated in the above are listed as follows:

1. Gingivitis
    Actinomyces forms including Actinomyces Israeli
    Coccus forms
2. Acute Necrotizing Ulcerative Gingivitis
    Spirochetes
    Bacteroides Intermedius
    Fusiform Nucleatum
3. Juvenile Periodontitis
    Actinobacillus Actinomycetumcomitans
    Capnocytophagia
    Bacteroides Intermedius
4. Adult periodontitis
    Bacteroides Gingivalis
    Bacteroides Intermedius
    Actinobacillus Actinomycetumcomitans
    Vibro Nucleatum
    Fusobactium Nucleatum
    Fusobactium Bacteroides
    Anaerobic Cocci Research has demonstrated that stabilized chlorine dioxide is lethal to Bacteriodes gingivalis and Actinobacillus Actinomycetumcomitans in vitro at the 95% level in twenty seconds with a 0.02% concentration. Research in vivo demonstrates that these organisms are significantly reduced or eliminated in humans when chlorine dioxide agent is applied to the pocket area using a syringe or water injection device with a needle to force penetration into the gingival crevices with the chlorine dioxide concentration in the range of 0.05% to 0.2%. Both gingivitis and periodontitis cause an increase in the rate of epithelial cells sloughing, aggravate oral malodor and cause some ulceration of tissue leaving the gingival bleeding; such bleeding is also reduced by treatment with a solution of stabilized chlorine dioxide through splitting of the di-sulphide bonds of hydrogen sulphide and methyl mercaptan.

Stabilized chlorine dioxide in aqueous solution is thus highly useful in the treatment of gingivitis, periodontitis and bleeding gingiva.

EXAMPLE V

Denture Soak

The malodors of the mouth result substantially from the volatile sulfur compounds which are present in saliva. Saliva coats and penetrates dental prosthetic devices including full dentures and partial dentures and forms an acquired pellicle. Further, food and other cellular debris adheres to dental prosthesis. Both anaerobic and aerobic bacteria accumulates on and in the microscopic faults and pores of these prosthetic devices for form a plaque matrix, as discussed above. Stabilized chlorine dioxide in aqueous solution has been demonstrated as a bactericide. It is also effective for neutralizing sulfur-based malodors, removing organic debris from dental prosthesis and as a disinfectant. As a dental soak the solution is antimicrobial, removes sulfur compounds and breaks down organic material and can be used in solution form having a concentration of from approximately 0.002% to 0.27%.

EXAMPLE VI

Cellular Debridement Agent

Many wounds and desquamative diseases such as Lichen Planus, Desquamative Gingivitis and desquamative dermatological disease are aided by organic debridement agents and antimicrobial agents. Solution or composition containing stabilized chlorine dioxide in aqueous solution in 0.05% to 0.1% and higher concentrations is effective to treat these problems. One particular application would be in veterinarian applications for the purpose of reducing odor attendant to these wounds and diseases.

EXAMPLE VII

Sanitizer And Cold Sterilization Agent

The known bacterial, fungicidal and viralcidal characteristics of chlorine dioxide also make it extremely useful as a sanitizer which can be a solution in which materials can be dipped or by application in an aerosol spray. The sanitizer can be used for food, sickroom use bathroom and cold sterilization of many instruments and pieces of equipment not generally amenable to autoclave sterilization. Again, the concentration of the stabilized chlorine dioxide would be preferably in the range of from 0.005% to 2.0%.

EXAMPLE VIII

Contact Lens Soak

Contact lenses accumulate bacteria and cellular debris from the eye. The known bactericidal, fungicidal and viralcidal capacity of stabilized chlorine dioxide along with its low toxicity makes stabilized chlorine dioxide solution an ideal lens soak. In addition, the capacity to degrade organic debris helps keep the lens clean and nonirritating. The preferred range of concentration is 0.005% to 0.2% in sterilized water.

It will be seen from the foregoing that stabilized chlorine dioxide in solution or as part of a composition or compound is effective in treating and preventing the formation of mouth malodor, inhibiting acquired pellicle and as a suitable plaque control agent, a bactericide, viralcide and fungicide superior to other compositions used today. Stabilized chlorine dioxide has been used for many years in other areas and extensive study in animals and in man have demonstrated its low toxicity and safety. Chlorine dioxide is approved by the Environmental Protection Agency for water purification, food preparation and preservation as well as a bacteriostatic, fungistatic and viralstatic agent.

I claim:

1. A method for retarding the formation of dental plaque caused by streptococcus sanguis bacteria, said method comprising the step of contacting said streptococcus sanguis bacteria within the oral cavity with 0.005% to 0.2% concentration of stabilized chlorine dioxide until the motility and mytotic activity of said streptococcus sanguis bacteria is reduced.

2. The method of claim 1 wherein the contacting step is performed for at least 10 seconds.

* * * * *

UNITED STATES PATENT AND TRADEMARK OFFICE
CERTIFICATE OF CORRECTION

PATENT NO. : 4,925,656
DATED : May 15, 1990
INVENTOR(S) : Ratcliff, Perry A.

It is certified that error appears in the above-indentified patent and that said Letters Patent is hereby corrected as shown below:

On the title page, Item [60]:

in line 4, after "continuation-in-part of", insert --each of--;

in line 5, after "4,689,215", insert --and Ser. No. 017,241, Dec. 29, 1986, Pat. No. 4,696,811, each of--;

in line 7, delete ", and", substitute --.--;

in line 8, delete line 8; and in line 9, delete line 9.

Signed and Sealed this

Eleventh Day of August 1998

*Attest:*

BRUCE LEHMAN

*Attesting Officer*  *Commissioner of Patents and Trademarks*